United States Patent [19]

Schoolman

[11] Patent Number: 5,052,411
[45] Date of Patent: Oct. 1, 1991

[54] VACUUM BARRIER ATTACHMENT FOR MEDICAL EQUIPMENT

[76] Inventor: Arnold Schoolman, 1000 E. 50th St., Ste. 310, Kansas City, Mo. 64110

[21] Appl. No.: 552,150

[22] Filed: Jul. 12, 1990

Related U.S. Application Data

[63] Continuation-in-part of Ser. No. 236,943, Aug. 26, 1988, abandoned.

[51] Int. Cl.⁵ ...................... A61B 17/56; A61B 17/16
[52] U.S. Cl. .................................... 128/863; 128/847; 606/80; 408/67
[58] Field of Search ...................... 433/91, 92; 408/67; 128/846, 847, 849, 850, 857, 303.13–303.19, 317, 329 R, 888, 863; 604/35; 606/115, 180, 79, 80

[56] References Cited

U.S. PATENT DOCUMENTS

| | | | |
|---|---|---|---|
| 2,305,289 | 12/1942 | Coburg | 128/850 |
| 3,537,447 | 11/1970 | Gauthier | 128/847 |
| 3,881,477 | 5/1975 | Von Otto | 128/847 |
| 3,936,213 | 2/1976 | Kappel | 408/67 |
| 4,037,982 | 7/1977 | Clement | 408/67 X |
| 4,055,173 | 10/1977 | Knab | 128/863 |
| 4,082,092 | 4/1978 | Foster | 128/847 |
| 4,140,105 | 2/1979 | Duvlis | 128/847 |
| 4,176,453 | 12/1979 | Abbott | 433/91 X |
| 4,184,226 | 1/1980 | Loevenich | 408/67 X |
| 4,223,669 | 9/1980 | Morledge | 128/847 |
| 4,228,798 | 10/1980 | Deaton | 604/320 X |
| 4,250,882 | 2/1981 | Adair | 128/888 |
| 4,252,054 | 2/1981 | Bakels | 433/92 |
| 4,446,861 | 5/1984 | Tada | 128/863 |
| 4,650,171 | 3/1987 | Howorth | 128/845 X |
| 4,652,184 | 3/1987 | Fischer | 408/67 |
| 4,662,802 | 5/1987 | Osterman | 408/67 |
| 4,719,914 | 1/1988 | Johnson | 128/303.14 X |
| 4,844,064 | 7/1989 | Thimsen et al. | 606/80 |

FOREIGN PATENT DOCUMENTS

| | | | |
|---|---|---|---|
| 2233125 | 6/1973 | Fed. Rep. of Germany | 408/67 |
| 2912396 | 10/1980 | Fed. Rep. of Germany | 408/67 |
| 2925908 | 1/1981 | Fed. Rep. of Germany | 408/67 |
| 2067106 | 7/1981 | United Kingdom | 408/67 |
| 81/02129 | 8/1981 | World Int. Prop. O. | 408/67 |

Primary Examiner—Robert A. Hafer
Assistant Examiner—Kevin G. Rooney
Attorney, Agent, or Firm—Litman, McMahon & Brown

[57] ABSTRACT

An attachment for use with medical tools to aid in isolating a medical practitioner from infectious materials found in a patient. The attachment includes both a physical barrier and means for providing a vacuum barrier around the tool to trap aerosols and the like developed by the tool during an operation. The barrier is flow connected to a vacuum source for drawing a vacuum, and gases drawn in by the source are collected by a filter. The barrier is transparent with radial spokes which form a ring-shaped passage or air channel to allow the practitioner to see the site of the operation and is disposable after each operation.

17 Claims, 1 Drawing Sheet

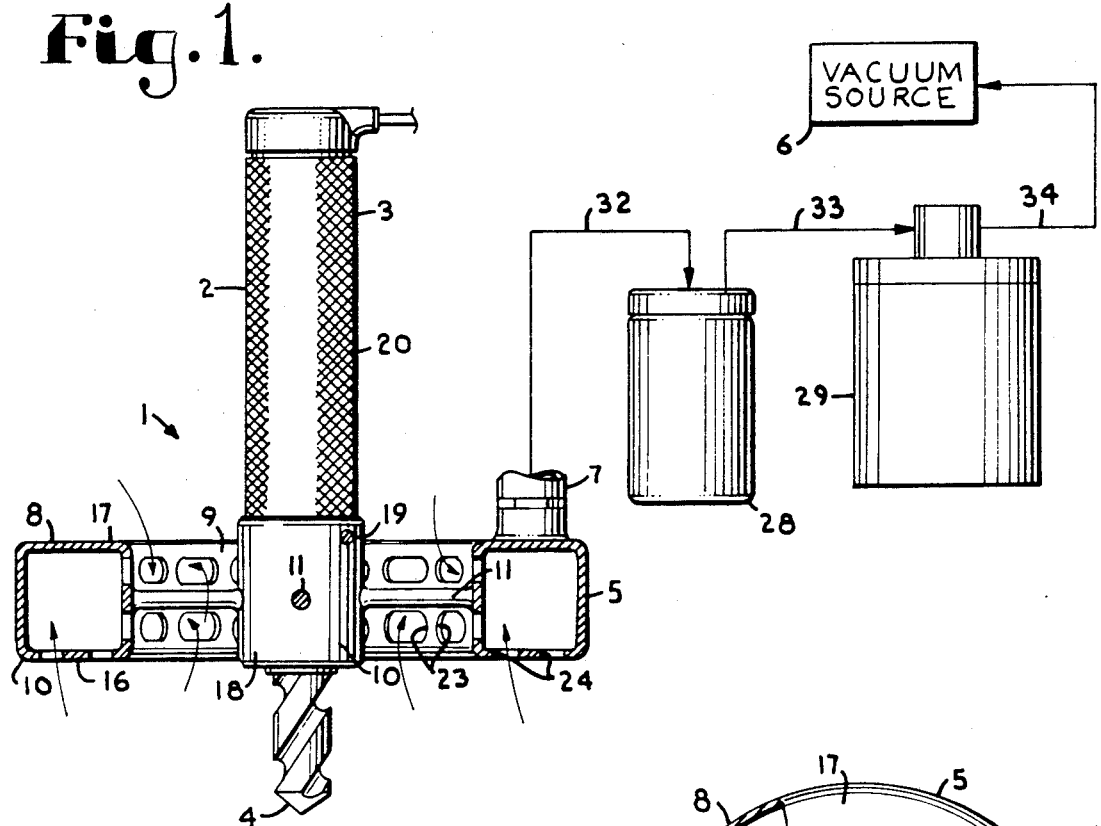
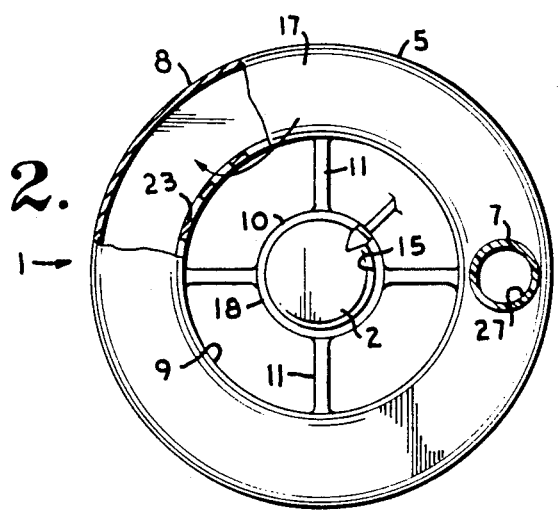
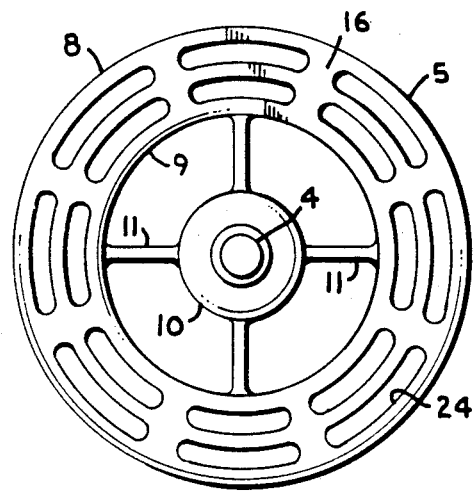
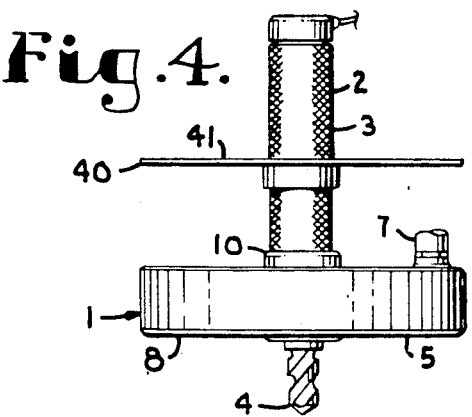

VACUUM BARRIER ATTACHMENT FOR MEDICAL EQUIPMENT

CROSS-REFERENCE TO RELATED APPLICATION

The present application is a continuation-in-part of parent application Ser. No. 07/236,943 filed Aug. 26, 1988, now abandoned, having the same title.

BACKGROUND OF THE INVENTION

The present invention relates to devices for shielding or protecting an operator of a medical tool from harmful aerosols, blood and other substances created during medical procedures and the like and, in particular, a combination vacuum and physical barrier attachment for such tools.

The medical community has long recognized the need to shield medical practitioners and patients from harmful substances, such as: noxious gases, infected body fluids, tissue debris and bone chips, produced in medical and dental procedures. Many previous systems have been designed to draw a vacuum in order to remove harmful substances eminating from a patient (for example, U.S. Pat. No. 3,537,447 of Gauthier). Still other systems have combined a vacuum source with a physical shield for added protection (for example, U.S. Pat. No. 4,650,171 of Howorth). Although the prior art systems provide the operator some protection, the recent acquired immunodeficiency syndrome (AIDS) epidemic has produced a need for providing greater protection for health care workers. The present technology is inadequate for this purpose.

In particular, medical procedures such as drilling, cutting with a reciprocating saw or the like which are common procedures for surgeons, especially orthopedic surgeons and neurosurgeons, produce an aerosol of human tissue that becomes suspended in the air around the site of the operation and which may contain AIDS virus, if the patient is infected. Such aerosols can come into contact with mucus membranes of medical personnel in the operating field and infect such personnel with the virus.

At the time of filing of the present application, it is estimated that AIDS has already claimed 28,000 lives in the United States and an estimated 1.5 million Americans have been infected by the human immunodeficiency virus (HIV). The virus which is transmitted through body fluids has been isolated in blood, semen, saliva, tears, urine, cerebrospinal fluid, cervical secretions, breast milk, bone and other tissues. There are reported cases of HIV infections acquired by health care workers in the workplace and it is estimated that the number of unreported cases is large. Several of these workers acquired the virus when infected body fluids or particles came in contact with exposed or uncovered mucous membranes or surfaces that were abraded, cut or otherwise open to allow the virus to penetrate the skin.

To shield health care workers from the AIDS virus, special precautions in the use of surgical and dental equipment should be taken. As was noted above use of such medical equipment often results in the release of AIDS or otherwise infected material from a patient into the surrounding air.

This is especially true in the use of medical drills, routers and saws which produce in the surrounding air a fine aerosol of fluids, tissue and bone chips or may even cause a stream of blood to spurt into the air. Similarly, endoscopes and other tubes inserted in patients for various medical procedures can result in the release into the surrounding air droplets or an aerosol of infected blood, saliva or other body fluids. Such airborn virus floats around the operating room and may encounter and invade a medical practioner in the room.

In light of the deadliness of the AIDS virus and the need to remove virtually all of the virus carrying aerosol produced in a medical procedure, present shielding systems are inadequate. Conventional barriers, whether physical or vacuum-producing, that are situated away from the operating tool either limit visibility and/or mobility or expose the operator to the possibly infected aerosol. When using surgical and dental equipment, a medical practitioner must often work between the vacuum source or physical barrier and the operating site, thus exposing the practitioner to infection or the barrier restricts the practitioner's view or movement of the tool.

Point of operation protection is needed without loss of mobility and/or visibility while maximizing protection. Vacuum barriers placed directly onto the operating surface are not well-suited to medical procedures and vacuum barriers positioned on the instrument itself typically limit the area of protection, as the vacuum only draws in air from the area nearest to the tool.

Existing physical shields are also inadequate. Such shields cannot be placed close enough to the operating site to provide effective protection without greatly reducing operator mobility and/or visibility and physical barriers do not remove the aerosol from the ambient air. Similarly, present shielding systems that combine a vacuum barrier with a physical shield are ineffective because the shield can become soiled and this in turn decreases visibility or the operator must work between the shield and the operating site to use the equipment. When using surgical equipment, the operator often must be able to move in many directions to get the correct point of contact or leverage to use the equipment. Additionally, present shielding cannot protect medical practitioners from spurts of blood because vacuum barriers are ineffective on such streams and physical barriers cannot be utilized without the aforementioned shortcomings.

SUMMARY OF THE INVENTION

The present invention provides a shielding apparatus or system which can be connected or attached to surgical and dental equipment so as to be positioned between the operator and the patient. The system includes a physical barrier to deflect possible contaminants away from the operator and a vacuum barrier spaced away from the equipment yet attached to it, to draw contaminants away from the operator. The operator is allowed full freedom of movement relative to holding and moving the tool, as the physical barrier is mounted on the tool in such a manner that the operator does not have to work under or around a prepositioned shield. Also, visibility of the operating site is maintained by constructing the physical barrier of transparent material, preferably clear plastic, and incorporating radial spokes spacing the main body of the apparatus from the tool so as to form an air channel, or ring-shaped passage, between the tool and the main body of the apparatus and thereby providing visibility even though the physical shield is soiled.

The air channel is constructed such that debris and aerosols passing into the air channel from the operating site are drawn by suction into the apparatus and away from the operator. This allows a clear view of the operational site by the user without the need for physical protection along the axis of the tool. In addition, the suction produced by the apparatus draws air down into the channel away from the operator's face and body, thereby creating a "vacuum barrier" to aerosols escaping from the operational procedure that otherwise would be allowed to reach the operator.

A secondary, solid physical shield may be mounted on the tool in spaced relation to the air channel and closer to the operator to protect from the occasional blood spurt which the vacuum barrier might not stop.

The specific design of the shield including the size, shape and method of attachment is somewhat dependent upon the particular tool for which the shield is to be used. Although specific designs will vary, each shield has at least one suction aperture directed to produce a suction between the operating site and the apparatus when in use and in flow communication with a vent. The vent is connected to a vacuum source through a flexible tube providing a vacuum at the suction aperture. Contaminants drawn in through the suction aperture can then be removed by a filter system connected to the vacuum source. The filter system also contains a solution of sodium hypochlorate, such as sold under the trademark "Clorox", through which pass the gases drawn by the vacuum system so as to further ensure that the gases exiting the system are disinfected. The apparatus is removably attached to the shield and except for the vacuum source such as a pump, is readily disposable by incinerator or the like in such a manner as to destroy any contamination therein.

OBJECTS OF THE INVENTION

The principal objects of the present invention are: to provide a shielding device including a combination physical barrier and vacuum barrier for use in shielding an operator of medical equipment or related tools from harmful substances produced in the use of the equipment; to provide such a device which will maintain adequate visibility and mobility of the operator of the equipment while increasing protection; to provide such a device which can be maintained in an operative position between the patient and the operator without overly interfering with the movements of the operator in using the equipment; to provide such a device which can be placed as close to the surgical or other medical site as possible to remove possible contaminants as soon as they are released; to provide such a device that offers a vacuum barrier that positively and effectively draws air away from an operator along a line of site of the operator with the surgical site so as to protect the operator from aerosols and other emissions from the site; to provide such a device which can be adapted for use with different types of surgical or dental equipment, and to provide such a device which is relatively inexpensive to manufacture, easy to set up and use and particularly well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a fragmentary side elevational and partly schematic view of a protective system including a vacuum barrier attachment mounted on a surgical drill in accordance with the present invention with portions broken away to show detail thereof.

FIG. 2 is a top plan view of the vacuum barrier attachment and drill with portions broken away to show detail thereof.

FIG. 3 is a bottom plan view of the vacuum barrier attachment and drill.

FIG. 4 is a side elevational view of a modified vacuum barrier attachment and drill on a reduced scale including a secondary physical barrier.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally represents a vacuum barrier attachment removably secured to a surgical drill 2 comprising a drill casing 3 and a drill bit 4 in accordance with the present invention. The vacuum barrier attachment 1 includes a primary vacuum producing and physical barrier 5, a vacuum source 6 and conduit means such as illustrated conduit assembly 7 flow connecting the vacuum source 6 to an interior of the primary barrier 5, as shown in FIG. 1. The primary barrier 5 is a hollowly constructed cylindrical wheel or ring 8 with a cylindrical inner surface 9 concentric with a hub 10.

The vacuum barrier attachment 1 includes at least one radial spoke 11 connecting the ring 8 to the hub 10. The hub 10 includes a longitudinal bore 15 passing axially therethrough. The bore 15 is sized to allow the hub 10 of the primary barrier 5 to slide over and surround the drill casing 3 in a closely spaced relation. The primary barrier 5 has a generally flat side or surface 16 directed towards a patient, when the attachment is in use, and a generally flat side or base 17 facing the operator. The ring 8 is spaced from the hub 10 and the drill casing 3 by the spokes 11.

The primary barrier 5 is mounted on the drill casing 3 so as to encircle the drill bit 4 and extend radially outward therefrom. Attachment means are provided to secure the primary barrier 5 in position relative to the drill casing 3. In the illustrated embodiment of FIGS. 1 to 3, the attachment means comprise a collar 18 having at least one set screw 19 threaded through the collar 18 and engageable with the drill casing 3, when the barrier 5 is positioned on the drill casing 11 and the screw 19 is tightened. The collar 18 extends from the base 17 of the primary barrier 5 so that the bore 15 extends axially therethrough. The hub 10 and the bore 15 define the collar 18.

When the primary barrier 5 is positioned on the surgical drill casing 3, as shown in FIG. 1, the primary barrier 5 is selectively held in place on the drill casing 3 by tightening the set screw 19 or removed for disposal by alternatively loosening the screw 19. The preferred material of construction of the primary barrier 5 is a transparent plastic that provides sufficient support to prevent collapse under the vacuum, but which allows the operator to see through to the site where the drill 2 is being utilized. The primary barrier 5 is positioned on the drill casing 3 so as to be positioned between the drill 4 and a grasping location or grip 20 on the casing 3. The grip 20 is held by the operator during use and allows the operator to manipulate the drill 2.

A first set of suction apertures 23, generally ovate and curved in shape, are arranged in a radially and circumferentially spaced matrix through the barrier surface 16 so that the first apertures 23 become increasingly wider as they progress radially outward, as is shown in FIG. 3. A second set of suction apertures 24, generally ovate and curved in shape, are arranged in a circumferentially spaced matrix on the cylindrical inner surface 9 of the primary barrier 5. A vent aperture 27 is placed in the barrier base 17, so that gas and other particles drawn in through the suction apertures 23 and 24 by vacuum therein travel through the hollow primary barrier 5 and out the vent aperture 27.

It is foreseen that other shaped configurations of the primary barrier 5 could be utilized keeping in mind that it is typically advantageous to have the suction apertures located or positioned so as to cover as much of the site of the operation as possible so as to act as a direct barrier by drawing aerosol away from the line of sight and also to collect as much of the aerosol released as possible, as a vacuum producing barrier. These variations include but are not limited to: a conically shaped physical and vacuum producing barrier, a latching mechanism used to easily and quickly attach and/or remove the physical barrier from the surgical drill, and tear shaped suction apertures arranged circumferentially around the physical barrier.

A collection bottle 28 and filter means such as filter system 29 are flow connected to the conduit assembly 7 so as to collect fluid between the primary barrier 5 and the vacuum source 6 to remove harmful substances drawn in through the suction apertures 23 and 24. The conduit assembly 7 comprises a first tube 32 connecting the primary barrier 5 to the collection bottle 28. The first tube 32 is flexible and sufficiently long enough to allow mobility in the use of the surgical drill 2. The vacuum source 6, filter 29 and bottle 28 may be located close to the operating arena or located in a separate room. A suitable vacuum source 6 is of the type sold by Renaii, Inc. under the trademark "Rainbow" having a disposable container for holding liquid such as a disinfectant. The conduit assembly 7 also includes a second tube 33 connecting the collection bottle 28 to the filter system 29 and a third tube 34 connecting the filter system 29 to the vacuum source 6. The filter system 29 includes therein a sodium hypochlorate solution for disinfecting the gases passing through the conduit assembly 29 before release of such gases to the ambient air.

The primary barrier 5, the conduit assembly tubes 32 and 33, the collection bottle 28 and the filter system 29 are preferably disposable after each usage to prevent the possibility of cross-contamination between patients.

FIG. 4 illustrates the addition of a secondary barrier attachment 40. The barrier attachment 40 includes a secondary physical barrier 41 located between the operator of the drill 2 and the primary barrier 5. The preferred material of construction of the secondary barrier 41 is a transparent plastic. The secondary barrier 41 is a relatively thin disc extending radially outward from the drill casing 3 and is mounted similarly to the primary barrier 5. The secondary barrier 41 preferably extends at least diametrically wide enough to equal the diameter of the ring-shaped passage or channel 42 between the hub 10 and the primary barrier 5.

It is foreseen that the secondary barrier 41 could be replaced by a hollow-construction physical barrier with suction apertures and vacuum producing means.

During use, the apertures 24 on the inner side of the ring 8 should allow virtually all gas and aerosols produced at the operative site to be drawn within the barrier 5, thereby protecting the user from contamination. Perhaps more importantly, the apertures 24 draw a continuous air flow from the user's direction along a line of site of the user with the operative site or drill bit 4 thereby creating a "vacuum barrier" with such air flow with respect to aerosols or other emissions from the operative site. During use, the operator may want to place a cloth shroud between the radially outer side of the barrier 5 and the patient to restrict flow of air in from this direction and increase flow of air from above the barrier 5 toward the channel between the ring 8 and the drill casing 3. In some instances, the user may wish to utilize tape or other suitable materials to further block flow of air around the bottom of the radially outer surface of the barrier 5.

In certain circumstances where the force behind contaminated particles may be too great so as to overcome the suction produced at the apertures 24, then the secondary barrier 41 may be utilized to insure the user is not contaminated.

Although the vacuum barrier attachment 1 described herein is for use with a surgical drill 2 it is foreseen that vacuum barrier attachments of varying design could be used with many types of surgical equipment, including but not limited to: endoscopes, routers, saws and endotracheal tubes. Also, the attachments could be used for tools in other hazardous environments besides operating rooms, for example, on tools used to drill or grind toxic metals, plastic or the like.

It is to be understood that while certain forms of the present invention have been illustrated and described herein, it is not to be limited to the specific forms or arrangement of parts described and shown.

What is claimed and desired to be secured by Letters Patent is as follows:

1. In a surgical drill having a drill bit rotatably mountable relative to a drill casing and having a user grasping region on said casing spaced from the bit for an operator to grasp said drill during use; the improvement comprising:

(a) an air flow directing and physical barrier removably mounted on said drill casing spaced from said drill bit so that said barrier encircles said drill casing but allows a user to visually see between said casing and said drill during use; said barrier extending radially outward from said drill and being located between said bit and said grasping region; said barrier including a cylindrical inner surface located in radially spaced relationship relative to said drill casing and including a plurality of suction apertures arranged in radially and circumferentially spaced relation around said barrier so as to open toward said drill and toward an operative site during use of said drill bit; and said barrier including support means to mount said barrier on said drill;
(b) a vacuum source adapted to draw a vacuum; and
(c) means for flow connecting said vacuum source with said suction apertures so that said vacuum source is adapted to draw gases through said apertures when said barrier attachment is in use.

2. The drill as set forth in claim 1 wherein:
(a) said barrier is concentrically mounted relative to said drill casing; and
(b) said barrier is transparent.

3. The drill as set forth in claim 1 further comprising:
(a) filter means in flow communication with said suction apertures for removing harmful substances from air drawn in through said suction apertures; and
(b) conduit means for connecting said filter means for removing harmful substances with said vacuum source.

4. The drill as set forth in claim 1 wherein said barrier is a primary barrier and including:
(a) a secondary physical barrier; said secondary barrier being a solid shield removably extending radially outward from said drill casing and being positioned between said primary barrier and the operator of said drill during use; and said secondary barrier being transparent.

5. The drill as set forth in claim 1 wherein:
(a) said barrier includes an outer ring; and
(b) said support means includes a hub directly attached to said drill casing and a plurality of spokes supporting said ring in radially outward spaced relationship relative to said hub.

6. A barrier attachment for use with a hand held surgical device comprising an equipment casing having a grasping region positioned thereon and a tool extending therefrom, said barrier attachment comprising:
(a) an air flow directing and physical barrier removably mounted on said tool casing spaced from said tool bit so that said barrier encircles said tool casing but allows a user to visually see between said casing and said tool during use; said barrier extending radially outward from said tool and being located between said bit and said grasping region; said barrier including a cylindrical inner surface located in radially spaced relationship relative to said tool casing and including a plurality of suction apertures arranged in radially and circumferentially spaced relation around said barrier so as to open toward said tool and toward an operative site during use of said tool bit; and said barrier including support means to mount said barrier on said tool;
(b) a vacuum source flow communicating with said apertures and adapted to draw gases through said apertures when said barrier attachment is in use;
(c) means for flow communicating said vacuum source with said apertures; and
(d) means for removably attaching said barrier to the surgical device so that said barrier is secured to the equipment casing between the tool and the grasping region so as to be spaced away from the surface on which the tool is to be used and so as to be spaced away from the surgical device, said attaching means include at least one radial spoke extending from said primary barrier to the surgical device.

7. The attachment as set forth in claim 6, wherein:
(a) said barrier is transparent and concentrically mounted relative to the surgical device; and
(b) in combination with the surgical device;
(c) whereby a working end of the tool is visible to an operator during use.

8. The attachment as set forth in claim 6 wherein:
(a) said barrier is a primary barrier; and
(b) a secondary physical barrier; said secondary barrier being a relatively thin disc removably mounted on the surgical device and extending radially outward therefrom; said disc being positioned between the operator and said primary barrier.

9. A barrier attachment for use with a surgical drill having a drill bit rotatably mountable relative to a drill casing and a grasping region on the drill casing for an operator to grasp the drill during use, said barrier attachment comprising:
(a) an air flow directing and physical barrier removably mounted on said drill casing spaced from said drill bit so that said barrier encircles said drill casing but allows a user to visually see between said casing and said drill during use; said barrier extending radially outward from said drill and being located between said bit and said grasping region; said barrier including a cylindrical inner surface located in radially spaced relationship relative to said drill casing and including a plurality of suction apertures arranged in radially and circumferentially spaced relation around said barrier so as to open toward said drill and toward an operative site during use of said drill bit; and said barrier including support means to mount said barrier on said drill;
(b) a vacuum source flow communicating with said apertures and adapted to draw gases through said apertures when said barrier attachment is in use;
(c) conduit means for flow communicating said vacuum source with said apertures; and
(d) attachment means for attaching said barrier to the drill so that said barrier is secured to the drill casing between the drill bit and the grasping region so as to be adapted to be spaced away from a surface to be drilled during use and so as to be spaced away from the drill, said attachment means include at least one radial spoke extending from said barrier to the drill casing.

10. The attachment as set forth in claim 9, wherein:
(a) said primary barrier is transparent and concentrically mounted relative to said surgical drill; and
(b) in combination with said surgical drill;
(c) whereby an operator can visibly see the drill bit during use.

11. The attachment as set forth in claim 9 further comprising:
(a) said barrier is a primary barrier; and
(b) a secondary physical barrier; said secondary barrier being a relatively thin disc removably mounted on the surgical device and extending radially outward therefrom; said disc being positioned between the operator and said primary barrier.

12. A barrier attachment for use with a hand held surgical device comprising an equipment casing having a grasping region positioned thereon and a tool extending therefrom, said barrier attachment comprising:
(a) an air flow directing and physical barrier removably mountable on the equipment casing between said tool and said grasping region so that said barrier is radially spaced from and encircles the equipment casing so as to allow a user to visually see between said barrier and said tool casing during use; said barrier having a ring including an inner surface facing said equipment casing and including a plurality of suction apertures therein;

(b) a vacuum source adapted to produce a vacuum during use;

(c) conduit means for flow communicating said vacuum source with said apertures in said barrier attachment;

(d) filter means removably connected to said conduit means between said vacuum source and said barrier attachment; and (e) attachment means for attaching said barrier attachment to the surgical device so that said barrier is secured to the equipment casing such that said barrier is spaced away from the surface on which the tool is to be used during use; said attachment means including at least one radial spoke extending from said barrier attachment to support means adapted to allow for relatively easy removal of said barrier attachment from the surgical device so as to provide for disposal of said barrier attachment and said filter means connected thereto after usage.

13. The attachment as set forth in claim 12 wherein:

(a) said barrier is a primary barrier; and (b) a secondary physical barrier; said secondary barrier being a solid and transparent relatively thin disc adapted to extend radially outward from the casing during use; said secondary barrier being adapted to be removably mounted to the equipment casing and positioned between the grasping region and said primary barrier to function to physically block particles passing between said primary barrier and the casing during use.

14. The attachment as set forth in claim 12 in combination with:

(a) said surgical device.

15. A barrier attachment for use with a surgical drill having a drill bit rotatably mountable relative to a drill casing and a grasping region on the drill casing for an operator to grasp the drill during use, said barrier attachment comprising:

(a) an air flow directing and physical barrier removably mountable on the equipment casing between said tool and said grasping region so that said barrier is radially spaced from and encircles the equipment casing so as to allow a user to visually see between said barrier and said tool casing during use; said barrier having a ring including an inner surface facing said equipment casing and including a plurality of suction apertures therein;

(b) a vacuum source adapted to produce a vacuum during use;

(c) conduit means for flow communicating said vacuum source with said apertures in said barrier attachment;

(d) filter means removably connected to said conduit means between said vacuum source and said barrier attachment; and (e) attachment means for attaching said barrier attachment to the drill so that said primary barrier is secured to the drill casing between the drill bit and the grasping region; said attachment means including at least one radial spoke extending between said barrier and the surgical device during use and adapted to allow for relatively easy removal of said barrier attachment from the drill to allow for disposal of said barrier attachment and said filter means connected thereto.

16. The attachment as set forth in claim 15 wherein:

(a) said barrier is a primary barrier; and (b) a secondary physical barrier; said secondary barrier being a solid and transparent relatively thin disc adapted to extend radially outward from the casing during use; said secondary barrier being adapted to be removably mounted to the equipment casing and positioned between the grasping region and said primary barrier to function to physically block particles passing between said primary barrier and the casing during use.

17. The attachment as set forth in claim 15 in combination with:

(a) said surgical drill.

* * * * *